US00PP37219P2

(12) United States Plant Patent
Huisman

(10) Patent No.: US PP37,219 P2
(45) Date of Patent: Jan. 20, 2026

(54) ***BRUNNERA* PLANT NAMED 'HBBM19'**

(50) Latin Name: *Brunnera macrophylla*
Varietal Denomination: HBBM19

(71) Applicant: Nico Huisman, Boskoop (NL)

(72) Inventor: Nico Huisman, Boskoop (NL)

(73) Assignee: HUISMAN BOOMKWEKERIJ B.V., Boskoop (NL)

( * ) Notice: Subject to any disclaimer, the term of this patent is extended or adjusted under 35 U.S.C. 154(b) by 0 days.

(21) Appl. No.: 19/274,554

(22) Filed: Jul. 19, 2025

(30) Foreign Application Priority Data

Apr. 24, 2025 (QZ) ..... PBR 20250872

(51) Int. Cl.
*A01H 6/00* (2018.01)
*A01H 5/02* (2018.01)

(52) U.S. Cl.
USPC ..... Plt./412

(58) Field of Classification Search
USPC ..... Plt./412
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Brunnera* plant named 'HBBM19' that is characterized by its flowers that are pink in color, its foliage that is solid green in color, and its spreading to spreading-upright plant habit.

2 Drawing Sheets

Botanical classification: *Brunnera macrophylla.*
Cultivar designation: 'HBBM19'.

CROSS REFERENCE TO A RELATED APPLICATIONS

This application claims priority to European Community Plant Variety Office (CPVO) Plant Breeder's Rights Application No. 2025/0872 filed on Apr. 24, 2025, under 35 U.S.C. 119(f), the entire contents of which is incorporated by reference herein. The information for the plant breeders' rights application was received directly from the Inventor.

BACKGROUND OF THE INVENTION

The present invention relates to a new and distinct cultivar of *Brunnera macrophylla* and is hereinafter referred to by the cultivar name 'HBBM19'. 'HBBM19' represents a new herbaceous perennial grown for use as a landscape plant.

The inventor discovered 'HBBM19' in April of 2019 as a seedling near a planting of an unnamed, unpatented *Brunnera macrophylla* proprietary selection that was growing in a trial field in Boskoop, The Netherlands. As the proprietary selection in the trial field was the only *Brunnera* planted in the area, it is believed to be self-pollinated, however the parentage cannot be certain.

Asexual propagation of the new cultivar was first accomplished under the direction of the Inventor by division in spring of 2019 in Boskoop, The Netherlands. Propagation by division and tissue culture using meristematic tissue has determined the characteristics to be stable and reproduced true to type in successive generations.

SUMMARY OF THE INVENTION

The following traits have been repeatedly observed and represent the characteristics of the new cultivar. These attributes in combination distinguish 'HBBM19' as a new and unique cultivar of *Brunnera.*

1. 'HBBM19' exhibits flowers that are pink in color.
2. 'HBBM19' exhibits foliage that is solid green in color.
3. 'HBBM19' exhibits a spreading to spreading-upright plant habit.

The probable parent plant of 'HBBM19' differs from 'HBBM19' in having white flowers. 'HBBM19' can be most closely compared to the cultivars 'Betty Bowring' (not patented) and 'Jack Frost' (U.S. Plant Pat. No. 13,859). 'Betty Bowring' is similar to 'HBBM19' in having green foliage and a spreading-upright plant habit. 'Betty Bowring' differs from 'HBBM19' in having white flowers. 'Jack Frost' is similar to 'HBBM19' in having a spreading-upright plant habit. 'Jack Frost' differs from 'HBBM19' in having blue flowers and dark green foliage that is heavily frosted with white.

BRIEF DESCRIPTION OF THE DRAWING

The accompanying colored photographs illustrate the overall appearance and distinct characteristics of the new *Brunnera*. The photographs were taken of a plant one year in age as grown outdoors in a 15 cm circular container.

The photograph in FIG. 1 provides a side view of 'HBBM19' in bloom.

Figure 1:
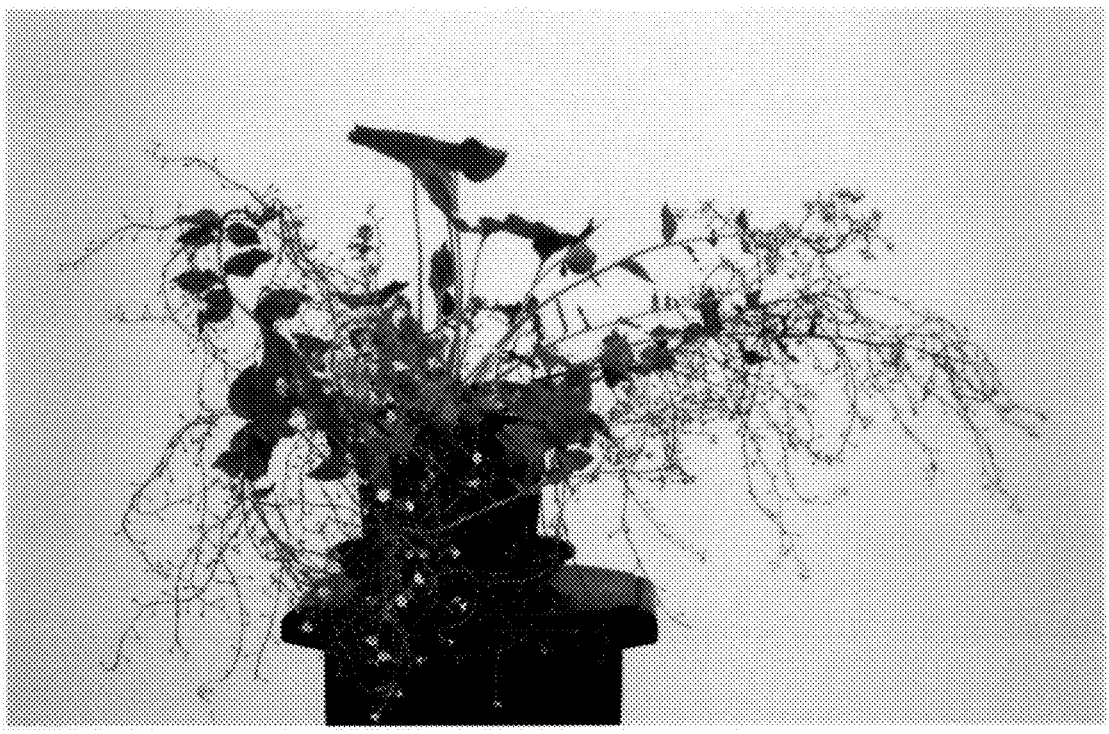
Figure 2:
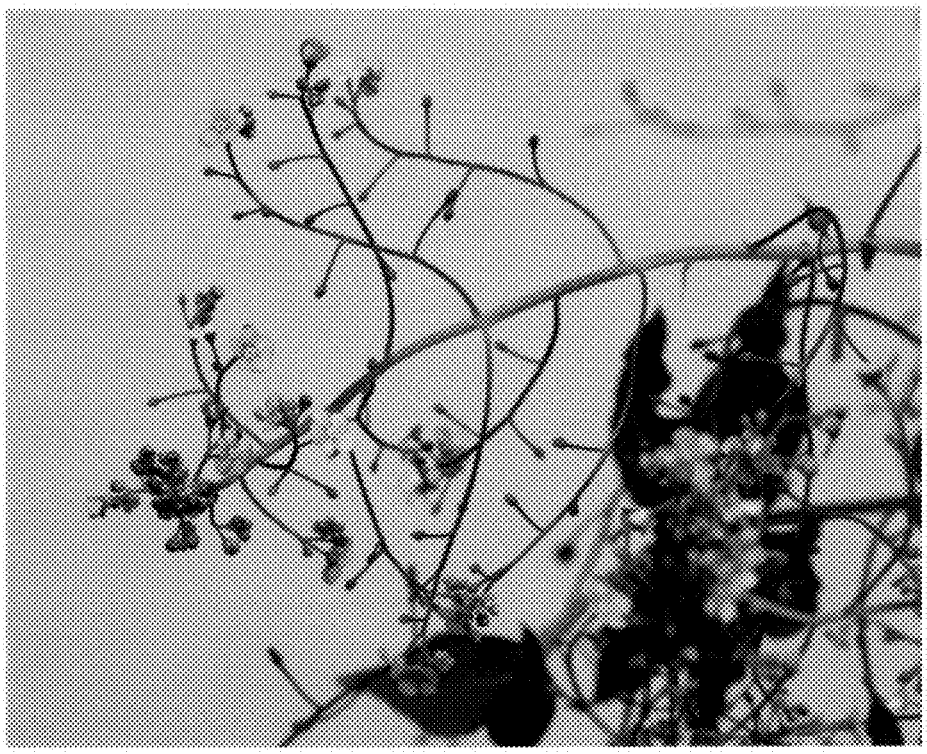

The photograph in FIG. 2 provides a close-up view of the flowers of 'HBBM19'.

Figure 3:
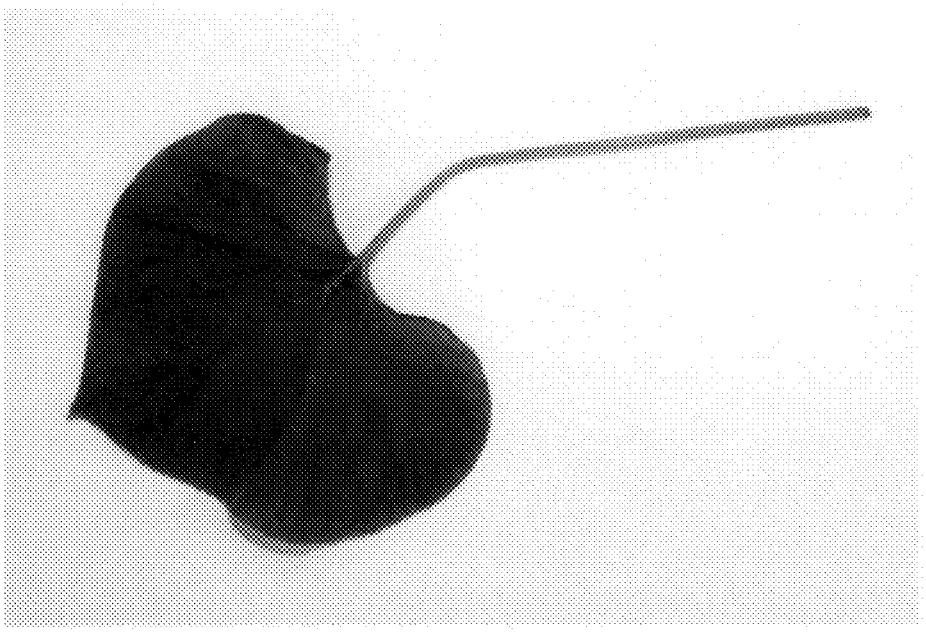

The photograph in FIG. 3 provides a close-up view of a leaf of 'HBBM19'.

The colors in the photographs are as close as possible with the photographic and printing technology utilized and the color values cited in the detailed botanical description accurately describe the colors of the new *Brunnera.*

DETAILED BOTANICAL DESCRIPTION OF THE PLANT

The following is a detailed description of one year-old plants of the new cultivar as grown outdoors in 15-cm containers in Boskoop, The Netherlands. The phenotype of the new cultivar may vary with variations in environmental, climatic, and cultural conditions, as it has not been tested under all possible environmental conditions. The color determination is in accordance with the 6th edition 2015, (2019 reprint) Colour Chart of The Royal Horticultural Society, London, England, except where general color terms of ordinary dictionary significance are used.

General description:

*Blooming period*.—April through May in The Netherlands.

*Plant type*.—Herbaceous perennial.

*Plant habit*.—Spreading to spreading-upright.

*Height and spread*.—Average of 22.4 cm in height and 68 cm in spread.

*Hardiness*.—At least hardy in U.S.D.A. Zones 3 to 9.

*Diseases and pests*.—No susceptibility or resistant to pests and diseases has been observed.

*Root description*.—Fibrous, medium in thickness and sparse in density.

*Branching habit*.—No lateral branches, leaves grow in basal rosettes, flowering stems arise from the centers of the rosettes before the mature leaves are formed.

*Propagation*.—Tissue culture and division.

*Root development*.—Time for root initiation is an average of 6 weeks, time to produce a fully rooted plant is an average of 5.5 months.

*Growth rate*.—Moderate to highly vigorous.

Branch description (flowering stems): None present, flowering stems grow from basal rosettes of leaves.

Foliage description:

*Leaf shape*.—Cordate.

*Leaf division*.—Single.

*Leaf base*.—Cordate.

*Leaf apex*.—Broad apiculate.

*Leaf venation*.—Pinnate-laciniate, veins furrowed, color upper surface; N144C, lower surface; 149D.

*Leaf margins*.—Entire, unlobed.

*Leaf attachment*.—Petiolate.

*Leaf arrangement*.—Basal rosettes.

*Leaf surface*.—Both surfaces matte, slightly rugose, moderately to densely pubescent, short adpressed, strigose hairs; 1 mm in length, N155A to 157D in color.

*Leaf variegation pattern*.—None.

*Leaf color*.—Young upper surface; 143A, young lower surface; 138A, mature upper surface; a blend of 144A and 146B, mature lower surface; a blend of 138C and 146C.

*Leaf size*.—Average of 11.9 cm in length and 12.2 cm in width.

*Leaf quantity*.—Average of 7 per rosette.

*Petioles*.—Average of 17.6 cm in length, 3 mm in width, both surfaces 144B in color and densely covered with short strigose hairs; 1 mm in length, N155A in color.

Flower description:

*Inflorescence type*.—Compound cyme.

*Inflorescence size*.—Average of 29 cm in height, 24.5 cm in diameter.

*Flower fragrance*.—None.

*Flower quantity*.—Average of 2,900 per plant, 300 per inflorescence.

*Flower lastingness*.—Average of one week, self-cleaning.

*Flower buds*.—Obovate in shape, 2 mm in length, 1.75 mm in diameter, color; 76A, immature sepals 144B, matte surfaces, covered with short strigose hairs; 0.2 mm in length.

*Flower aspect*.—Held in multiple angles.

*Flower size*.—Average of 8 mm in diameter, 2 mm in depth, throat diameter 0.5 mm, tube; 1 mm in length, 1.5 mm in diameter.

*Petals*.—Rotate, average of 5, 1 whorl, 3.5 mm in length and 3 mm in width, broadly obovate in shape, fused into a tube, entire margins, rounded apex, both surfaces are smooth, glabrous, velvety, and matte, color; when opening upper surface 76A, when opening lower surface a blend of 76B and 77D, when fully open upper surface 76B, when fully open lower surface a blend of 76B and 76C, veins 76B, throat color N155A, tube color 155C.

*Calyx*.—Campanulate, about 1.5 mm in width and 2 mm in length.

*Sepals*.—5, campanulate, lanceolate in shape, 1.5 mm in length, 0.5 mm in width, entire margins, narrow ovate apex, cuneate and fused base, upper surface matte, smooth and glabrous, lower surface very slightly glossy, moderately pubescent covered with very strigose hairs 0.2 mm in length, both surfaces 144B in color.

*Peduncles*.—Terminal peduncle, 45.4 cm in length, 3.5 mm in diameter, strong, angle; when developing in an average angle of 10°, when maturing peduncle flops to an average angle of 75°, color; 146B, upper surface tinged 152A to 152B, surfaces are slightly glossy, moderately covered with short strigose hairs; 1 mm in length, N155A in color.

*Pedicels*.—5 mm in length, 0.5 mm in diameter, moderately strong, held in a 45° angle, 145A in color, surfaces are matte, moderately covered with short strigose hairs; 0.2 mm in length.

*Floral bracts*.—Flowering stems leafy, alternate, average number of leaves per stem: 13, ovate in shape, average of 4 cm in length, average of 2 cm in width, entire margins, both surfaces matte and pubescent, color; upper surface a blend of 143A and 146B, lower surface 138B.

Reproductive organs:

*Gynoecium*.—Pistil; 1, 0.3 mm in length, stigma; club-shaped, 0.2 mm in diameter, 147A in color, style; 0.2 mm in length, 146B in color, ovary; 146B in color.

*Androecium*.—Stamens; 5, anthers; basifixed, broadly elliptic in shape, 0.5 mm in length, 0.4 mm in diameter, 203A in color, filaments; 0.5 mm in length and NN155D in color, pollen is low in quantity and 155D in color.

*Seed*.—No fruits or seed have been observed to date.

It is claimed:

1. A new and distinct cultivar of *Brunnera* plant named 'HBBM19' as herein illustrated and described.

* * * * *